(12) United States Patent
Mao et al.

(10) Patent No.: US 8,622,918 B1
(45) Date of Patent: Jan. 7, 2014

(54) METHOD FOR MONITORING VIABILITY OF TISSUE FLAPS

(75) Inventors: Jimmy Jian-min Mao, Fremont, CA (US); Robert E. Lash, Redwood City, CA (US)

(73) Assignee: ViOptix, Inc., Fremont, CA (US)

( * ) Notice: Subject to any disclaimer, the term of this patent is extended or adjusted under 35 U.S.C. 154(b) by 0 days.

(21) Appl. No.: 12/689,138

(22) Filed: Jan. 18, 2010

Related U.S. Application Data

(63) Continuation of application No. 11/162,380, filed on Sep. 8, 2005, now Pat. No. 7,657,293.

(51) Int. Cl.
*A61B 5/02* (2006.01)
(52) U.S. Cl.
USPC ............ 600/500; 600/310; 600/324; 600/323
(58) Field of Classification Search
USPC ............... 600/473–481, 483, 485, 490–504, 600/323–340
See application file for complete search history.

(56) References Cited

U.S. PATENT DOCUMENTS

| | | | |
|---|---|---|---|
| 3,256,151 A | 6/1966 | Douglas et al. | |
| 5,152,296 A | 10/1992 | Simons | |
| 5,285,783 A | 2/1994 | Secker | |
| 5,524,617 A * | 6/1996 | Mannheimer | 600/323 |
| 5,701,902 A | 12/1997 | Vari et al. | |
| 5,716,981 A | 2/1998 | Hunter et al. | |
| 5,779,631 A | 7/1998 | Chance | |
| 5,865,738 A * | 2/1999 | Morcos et al. | 600/365 |
| 5,931,779 A | 8/1999 | Arakaki et al. | |
| 6,064,899 A * | 5/2000 | Fein et al. | 600/323 |
| 6,587,701 B1 * | 7/2003 | Stranc et al. | 600/310 |
| 6,763,256 B2 | 7/2004 | Kimball et al. | |
| 2002/0035317 A1 * | 3/2002 | Cheng et al. | 600/322 |
| 2003/0065269 A1 * | 4/2003 | Vetter et al. | 600/503 |
| 2003/0087878 A1 | 5/2003 | Vinten-Johansen et al. | |
| 2004/0072183 A1 * | 4/2004 | Olsson et al. | 435/6 |
| 2004/0116814 A1 | 6/2004 | Stranc et al. | |

FOREIGN PATENT DOCUMENTS

WO 9844839 10/1998

OTHER PUBLICATIONS

Kamolz, L.P. et al., "Continuous Free-Flap Monitoring with Tissue-Oxygen Measurements: Three-Year Experience," Journal of Reconstructive Microsurgery, vol. 18, No. 6, Aug. 2002, pp. 488-491, Thieme Medical Publishers.

Thorniley, M.S., et al., "The Use of Near-Infrared Spectroscopy for Assessing Flap Viability During Reconstructive Surgery," British Journal of Plastic Surgery, vol. 51, 1998, pp. 218-226.

* cited by examiner

*Primary Examiner* — Michael D'Angelo
(74) *Attorney, Agent, or Firm* — Aka Chan LLP

(57) ABSTRACT

Methods and apparatus are used to assess the viability of tissue such as flap tissue. According to one aspect of the present invention, a method for assessing the viability of flap tissue includes obtaining an oxygen saturation level associated with a first location on the flap tissue, determining whether the oxygen saturation level is less than a first level, and identifying the first location as having a poor blood supply if the oxygen saturation level is less than the first level.

10 Claims, 8 Drawing Sheets

METHOD FOR MONITORING VIABILITY OF TISSUE FLAPS

CROSS-REFERENCE TO RELATED APPLICATIONS

This patent application is a continuation of U.S. patent application Ser. No. 11/162,380 filed Sep. 8, 2005, which is incorporated by reference along with all other reference cited in this application.

BACKGROUND OF THE INVENTION

1. Field of Invention

The present invention relates generally to optical imaging systems that monitor oxygen levels in tissue. More specifically, the present invention relates to monitoring oxygen levels to determine the viability of flaps before and after a flap transplant.

2. Description of the Related Art

Flap surgery is a type of plastic or reconstructive procedure that enables tissue from one area of a body to effectively be moved to another area of the body. A flap is a section of living tissue with a blood supply that may be transported from a "donor" area of a body to a new area of the body, i.e., an area onto which the flap is to be transplanted. A flap may be transplanted to an area of the body that has lost, for example, skin, fat, or muscle. Flap surgery generally restores some muscle movement or skeletal support to an area in which muscle movement or skin coverage may have been missing.

There are many different kinds of flaps that are used in flap surgery. A local flap is typically a piece of skin with underlying tissue that is located next to a wound. The local flap is repositioned over the wound while remaining attached at one end such that the local flap may be nourished by its original blood supply. A regional flap is generally a section of tissue that is attached by a specific blood vessel or specific blood vessels. When lifted, the regional flap uses a relatively narrow attachment to the donor, or original, site to receive a blood supply from the specific blood vessel or vessels, e.g., a tethered artery and vein. A musculocutaneous flap, i.e., a muscle and skin flap, is typically used when an area to be covered by the flap is relatively large and requires a significant blood supply. A musculocutaneous flap is often used in breast reconstruction surgery, and remains tethered to its original blood supply. A microvascular free flap is a flap of tissue and skin that is detached, along with blood vessels, from an original site of a body and reattached to a new site in the body. As a microvascular free flap is completely detached from an original site, the attachment of such a flap to a new site requires reattaching severed blood vessels at the new site.

Blood flow through transplanted flaps may change drastically in the period of time substantially immediately after a transplant is completed. A transplanted flap may sometimes die, i.e., transplanted tissue may die, when the blood flow through the transplanted flap is compromised. For example, a blood clot in the transplanted flap or a pinched vein in the transplanted flap may cause the transplanted flap to die. Currently, to monitor a transplanted flap to determine whether blood flow through a transplanted flap is adequate to sustain the transplanted flap, laser Doppler flap monitoring may be used. Laser Doppler flap monitoring, or laser Doppler flowmetry, allows Doppler measurements to be made near blood vessels of the transplanted flap. Interpretation of the Doppler measurements may enable potential flap failures to be detected before clinical signs of failure, e.g., discoloration of the transplanted flaps, manifest themselves.

Though laser Doppler flap monitoring may be effective for enabling potential flap failures to be detected in some instances, laser Doppler systems are generally able to make measurements on relatively large vessels, and are unable to measure regional perfusion in the micro-vasculature within a skin flap. Even though flow may be detected in larger vessels when laser Doppler flap monitoring is employed, distal flap tissue may be underperfused and, as a result, may die.

As an alternative to laser Doppler flap monitoring, some surgeons may nick a transplanted flap in various places to assess the blood flow therethrough. Nicking a transplanted flap is invasive and does not always allow for an accurate determination of the viability of a transplanted flap, as assessing the blood flow in such a manner is highly subjective. Further, it may be very difficult to determine where in a transplanted flap to make a nick, e.g., a surgeon may inadvertently fail to make a nick near a blood vessel that is pinched.

Therefore, what is needed is a method and an apparatus which allows the viability of a transplanted flap to be accurately determined. That is, what is desired is a system which is non-invasive and relatively non-subjective, and allows the blood flow through a flap to be accurately assessed.

BRIEF SUMMARY OF THE INVENTION

The present invention relates to assessing the viability of tissue such as flap tissue. According to one aspect of the present invention, a method for assessing the viability of flap tissue includes obtaining an oxygen saturation level associated with a first location on the flap tissue, determining whether the oxygen saturation level is less than a first level, and identifying the first location as having a poor blood supply if the oxygen saturation level is less than the first level.

In one embodiment, if the first location is identified as having a poor blood supply, then the tissue at and around the first location may be trimmed to substantially preserve the viability of the remainder of the flap. In another embodiment, the method also includes placing a sensor head of an optical imaging system in contact with the flap tissue at the first location such that the sensor head causes light to be reflected off of the flap tissue to allow the oxygen saturation level to be determined.

Measuring oxygen saturation levels associated with a flap may facilitate the identification of regions of a flap that may not be viable, or may not remain viable. The ability to identify areas that are either not viable or not likely to remain viable enables corrective action. Additionally, if oxygen saturation levels are measured in a potential flap before the potential flap is removed for transplant, arteries that are determined to provide significant blood flow to the potential flap may be readily identified as reattachment arteries.

According to another aspect of the present invention, a method for characterizing an artery that provides blood to flap tissue includes identifying a first oxygen saturation level associated with the flap tissue, and inhibiting a flow of blood through the artery to the flap tissue. The method also includes identifying a second oxygen saturation level associated with the flap tissue after inhibiting the flow of blood, and determining whether the second oxygen saturation level is significantly different from the first oxygen saturation level. If it is determined that the second oxygen saturation level is significantly different from the first oxygen saturation level, the artery is identified as providing significant blood to the flap tissue.

In one embodiment, identifying the artery as providing significant blood to the flap tissue includes cutting the artery and identifying the artery as a reattachment artery. In another embodiment, inhibiting the flow of blood through the artery includes clamping the artery to cut off a supply of blood through the artery.

According to still another aspect of the present invention, a method for identifying a location at which to obtain measurements of oxygen saturation levels includes positioning a sensor head at a first location. The sensor head is coupled to at least a first detector, a second detector, and a first source. The method also includes obtaining a first optical measurement and a second optical measurement using the sensor head. The first optical measurement is associated with the first detector when the first source emits light that is reflected into the first detector. The second optical measurement is associated with the second detector when the first source emits light that is reflected into the second detector. Finally, the method also includes determining whether at least a first ratio of the first optical measurement to the second optical measurement is approximately equal to one, and identifying the first location as the location at which to obtain the measurements of oxygen saturation levels if it is determined that the first ratio of the first optical measurement to the second optical measurement is approximately equal to one.

In accordance with yet another aspect of the present invention, a method for assessing viability of a tissue structure includes obtaining an oxygen saturation level associated with a first location on the tissue structure, and determining whether the oxygen saturation level is within a predetermined range. The method also includes identifying the first location as having an insufficient oxygen saturation level if the oxygen saturation level is not within the predetermined range. In one embodiment, the method further includes placing a sensor head of an optical imaging system in contact with the tissue structure at the first location. Such a sensor head causes light to be reflected off of the tissue structure to identify the oxygen saturation level.

These and other advantages of the present invention will become apparent upon reading the following detailed descriptions and studying the various figures of the drawings.

Other objects, features, and advantages of the present invention will become apparent upon consideration of the following detailed description and the accompanying drawings, in which like reference designations represent like features throughout the figures.

BRIEF DESCRIPTION OF THE DRAWINGS

The invention may best be understood by reference to the following description taken in conjunction with the accompanying drawings in which.

DETAILED DESCRIPTION OF THE INVENTION

Figure 1A:
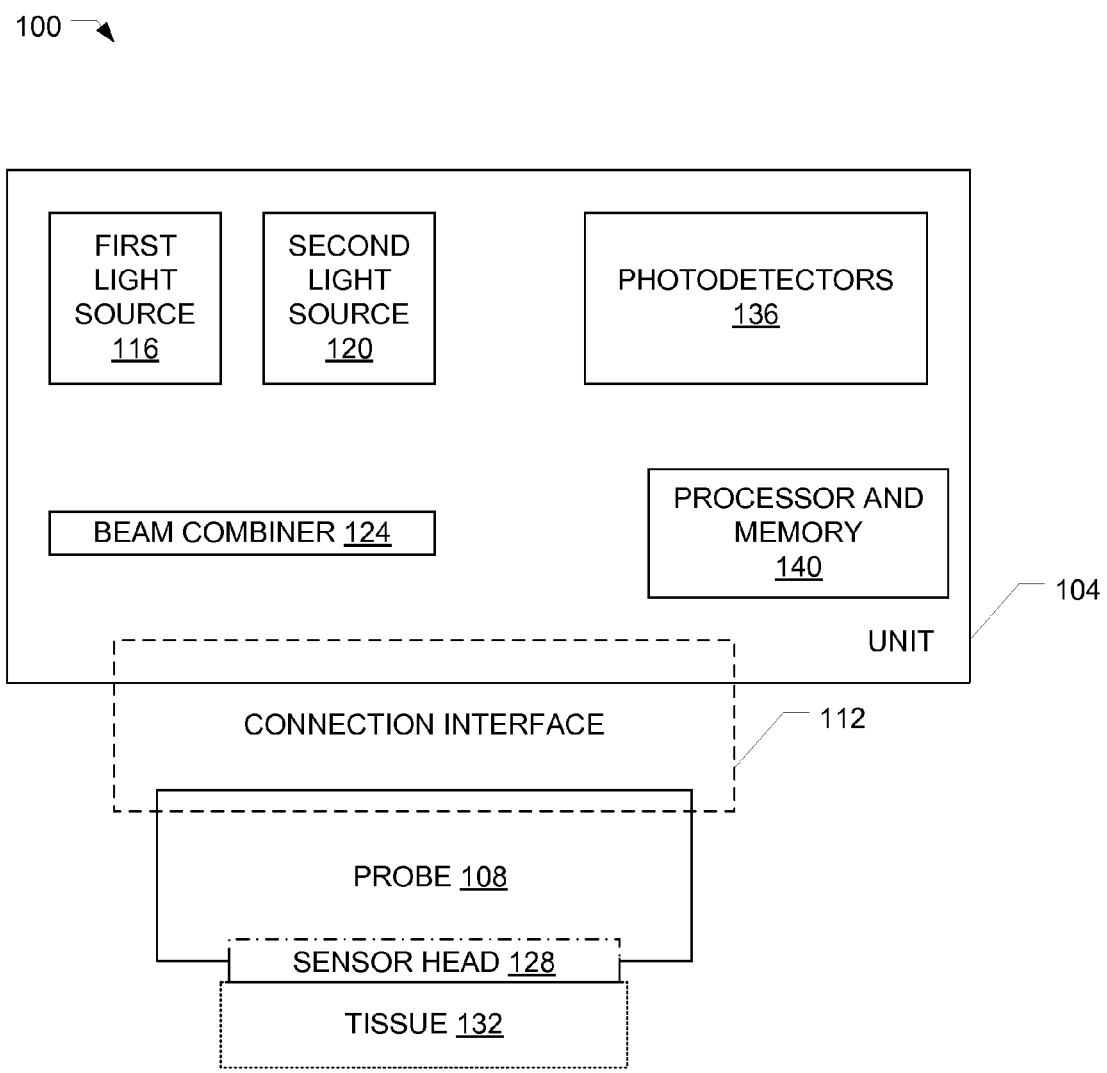
FIG. 1A is a block diagram representation of an optical imaging system that is suitable for use in monitoring flap tissue in accordance with an embodiment of the present invention.

Assessing the blood supply associated with a flap is crucial to ensure that the flap is viable. By monitoring the oxygen saturation level of an area on flap tissue, the blood flow to at least that area may be determined. Monitoring an oxygen saturation level is generally a non-invasive, non-subject process. Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobins are the dominant chromophores in the spectrum range of approximately 700 nm to approximately 900 nm. Accordingly, the near-infrared spectroscope has been applied to measure oxygen levels in the physiological medium such as tissue hemoglobin oxygen saturation and total hemoglobin concentrations.

Optical Diffusion Imaging and Spectroscopy (ODIS) allows tissue to be characterized based on measurements of photon scattering and absorption. In tissue such as human tissue, near infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source which emits the light and a detector which detects the light allows a depth of measurement to be determined. A ratio of oxyhemoglobin and deoxyhemoglobin may be used to allow for substantially real-time measurement of oxygen, e.g., oxygen saturation levels. A percentage of hemoglobin that is bound to oxygen may express an oxygen saturation level.

In one embodiment, measuring oxygen saturation levels associated with a flap may enable a surgeon to accurately identify areas of a flap that may not be viable. Being able to identify areas that are not viable enables corrective actions to be taken substantially before the integrity of the overall flap is compromised. By way of example, a surgeon may be able to trim tissue from areas of a flap that may not be viable in an effort to preserve the integrity of the remainder of the flap. In addition, if oxygen saturation levels are measured in a potential flap before the potential flap is removed for transplant, arteries that provide significant blood flow to the potential flap may be identified and, hence, designated for use as reattachment arteries.

FIG. 1A is a block diagram representation of an optical imaging system that allows oxygen saturation levels to be measured in accordance with an embodiment of the present invention. An optical imaging system 100 includes a unit 104 and a probe 108 that are coupled via a connection interface 112. Connection interface 112 is generally a light-tight interconnection with a laser safety interlock that is arranged to substantially prevent laser light from being emitted through connection interface 112 when probe 108 is not coupled to unit 104. Connection interface 112 typically includes a panel connector (not shown) attached to unit 104 and a cable connector (not shown) attached to probe 108.

Unit 104 includes a first light source 116 and a second light source 120. First light source 116 and second light source 120, in the described embodiment, are each dual wavelength light sources. In other words, first light source 116 provides two wavelengths of light and second light source 120 provides two wavelengths of light. First light source 116 and second light source 120 may each include a laser diode that provides a light beam or pulse at a lower frequency and a laser diode that provides a light beam or pulse at a higher frequency. By way of example, first light source 116 and second light source 120 may each include a laser diode that produces visible red light of an approximately 690 nanometer (nm) wavelength and a laser diode that produces near infra red light of an approximately 830 nm wavelength. It should be appreciated, however, that the wavelengths of light produced by laser diodes associated with first light source 116 and second light source 120 may vary widely.

Light emitted by first light source 116 and light emitted by second light source 120 is provided to a beam combiner 124 via optical fibers (not shown). Each laser diode associated with first light source 116 and each laser diode associated with second light source 120 is provided on a separate optical fiber (not shown). Beam combiner 124 effectively merges the light from the laser diodes of first light source 116 and merges the light from the laser diodes of second light source 120. The merged light is then provided via output fibers (not shown) to connection interface 112. The output fibers are arranged to allow the merged or combined light to be homogenized to ensure that the light is substantially uniformly distributed across the output fibers when the light enters connection interface 112.

Through connection interface 112, light is provided to a sensor head 128 of probe 108. Within sensor head 128, optical fibers (not shown) provide the merged light associated with first light source 116 and the merged light associated with second light source 120 to a surface of sensor head 128 that is arranged to come into contact with tissue 132.

When sensor head 128 causes light to be transmitted into tissue 132, the reflected light is collected by optical detector fibers (not shown) that are coupled to photodetectors 136. In general, at least two photodetectors 136 are included within unit 104 and are configured to be sensitive to the light which is transmitted by first light source 116 and second light source 120. A processor and memory 140, e.g., a component that is suitable for storing and executing computer software code devices or firmware code devices, within unit 104 is generally arranged to substantially determine an oxygen saturation level of tissue given reflected light collected by photodetectors 136.

Figure 1B:
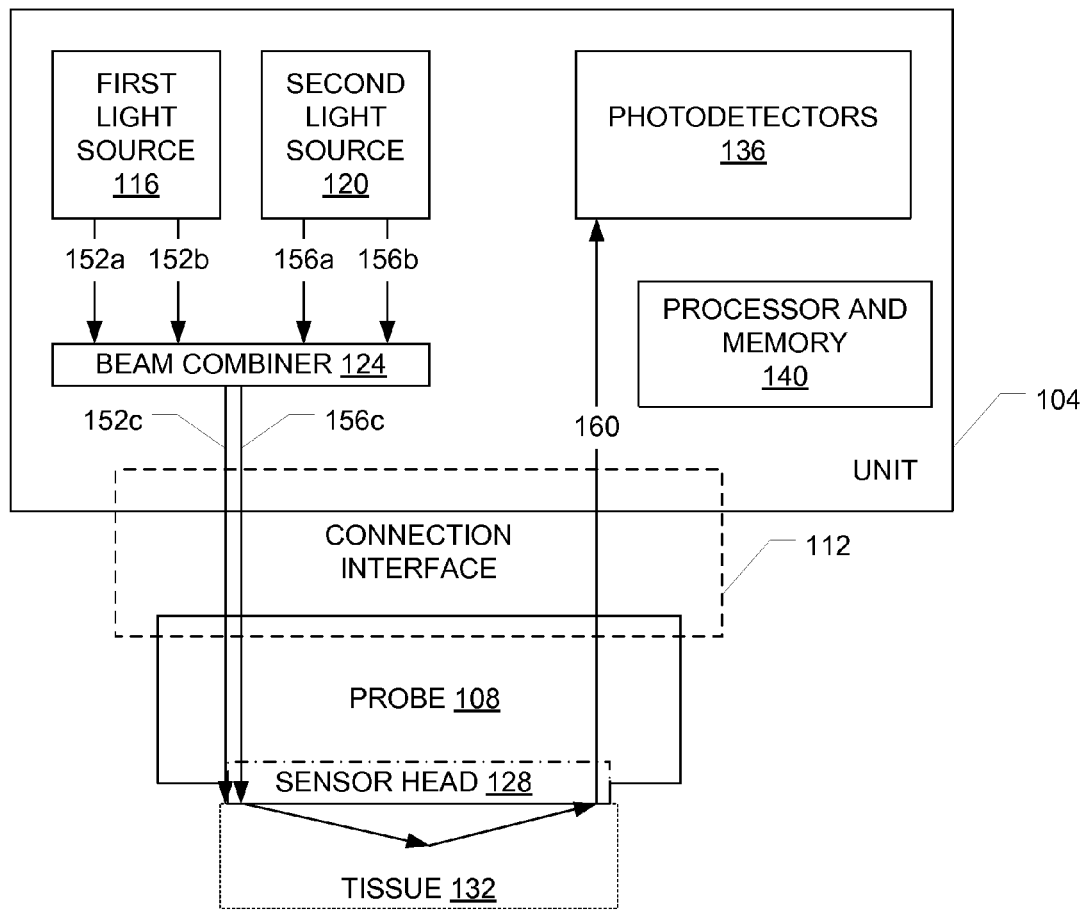
FIG. 1B is a block diagram representation of an optical imaging system that is suitable for use in monitoring flap tissue, i.e., optical imaging system 100 of FIG. 1A, in accordance with an embodiment of the present invention.

FIG. 1B is a block diagram representation of optical imaging system 100 of FIG. 1A which shows the path of light emitted by light sources, i.e., first light source 116 and second light source 120 of FIG. 1A, in accordance with an embodiment of the present invention. When first light source 116 emits light at two wavelengths, light of the first wavelength 152a and light of the second wavelength 152b are provided to beam combiner 124 which effectively merges the light into a light stream 152c that is provided to sensor head 128, e.g., through optical source fibers. Similarly, when second light source 120 emits light at two wavelengths, light of the first wavelength 156a and light of the second wavelength 156b are merged into a light stream 156c by beam combiner 124 that is provided to sensor head 128. Light streams 152c, 156c are transmitted into tissue 132 reflect off of tissue 132, through sensor head 128 to photodetectors 136.

Figure 2A:
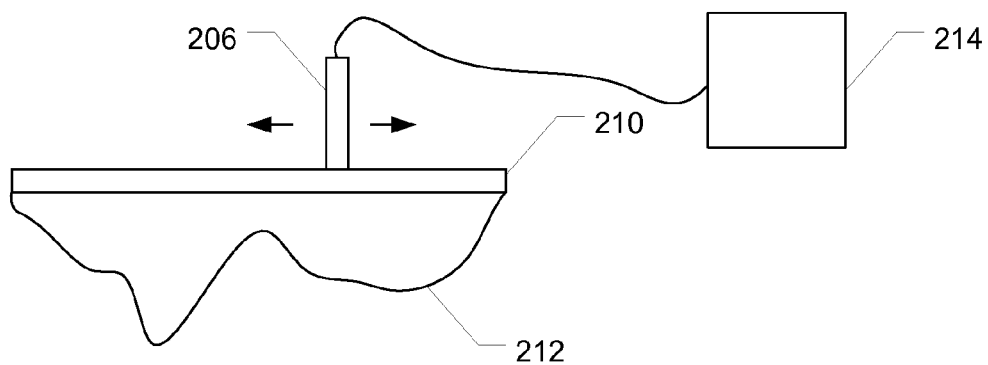
FIG. 2A is a diagrammatic representation of a probe of an optical imaging system being used to monitor flap tissue in accordance with an embodiment of the present invention.
Figure 2B:
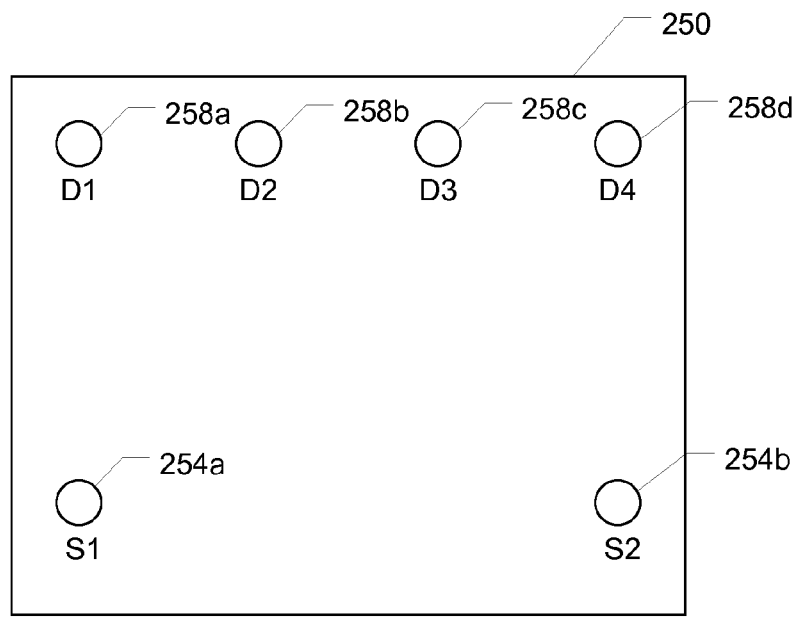
FIG. 2B is a diagrammatic representation of an orientation of optical fibers associated with optical sources and detectors in a sensor head of a probe in accordance with an embodiment of the present invention.

As shown in FIG. 2A, a probe 206 with a sensor head may be arranged to contact tissue 210 with underlying layers or structures 212 that may include, but are not limited to, bone and blood vessels. Probe 206, which is coupled to a unit 214 that is arranged to process information obtained by the sensor head of probe 206, may be moved over tissue 210 to allow oxygen saturation levels at different locations on tissue 210 to be assessed. The sensor head contains optical fibers that are coupled to sources and detectors. In general, the number of sources and detectors, as well as the orientation of sources and detectors, may vary. FIG. 2B is a representation of an orientation of optical fibers that are coupled to sources and detectors in accordance with an embodiment of the present invention. A sensor head 250 includes source fibers 254a, 254b and detectors fibers 258a-d. Although two source fibers 254a, 254b and four detector fibers 258a-d are shown, it should be appreciated that the number of source fibers and detector fibers may vary widely. The positioning of source fibers 254a, 254b relative to detector fibers 258a-d may also vary, e.g., source fibers 254a, 254b may generally have either a symmetric or a non-symmetric orientation with respect to detector fibers 258a-d. In general, as previously mentioned, light provided through source fibers 254a, 254b reflects off of tissue and underlying layers when sensor head 250 is in contact with a surface of the tissue. Once the light reflects, the reflected light is gathered by detector fibers 258a-d.

Underlying structures such as underlying structures 212 as shown in FIG. 2A may affect oxygen saturation level readings. By way of example, if the area under a particular portion of tissue 210 or if the particular portion of tissue 210 itself is not relatively homogenous, the accuracy of oxygen saturation level readings taken at that particular portion may be compromised. Hence, avoiding relatively significant tissue heterogeneity when taking readings of oxygen saturation level readings may be desirable.

Figure 3:
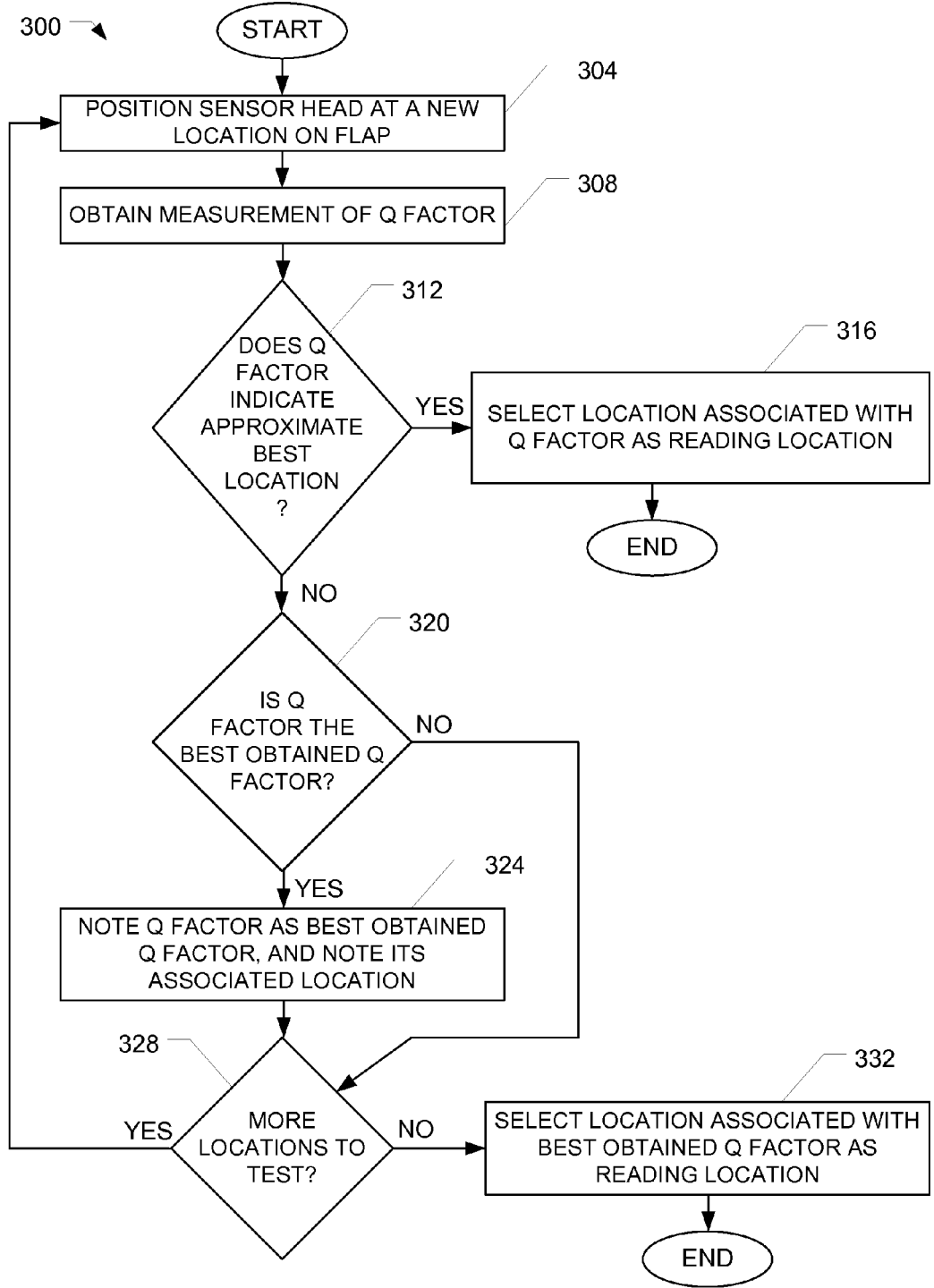
FIG. 3 is a process flow diagram which illustrates one method of utilizing an oximeter to determine a best location to use for monitoring oxygen levels in flap tissue in accordance with an embodiment of the present invention.

Identifying a substantially best location at which to measure oxygen saturation levels may reduce the likelihood that relatively significant tissue heterogeneity has an adverse affect on the oxygen saturation level measurements. With reference to FIG. 3, one method of identifying a location, i.e., a substantially best location, for obtaining oxygen saturation level readings will be described in accordance with an embodiment of the present invention. A process 300 of identifying a location begins at step 304 in which a sensor head is positioned at a location on flap. It should be appreciated that although the flap may generally be a transplanted flap, the flap may instead be a potential flap which has not yet been procured. Additionally, in lieu of a flap, the tissue onto which a sensor head is positioned may instead be a transplanted digit.

Once the sensor head is positioned at a location, light is sent through the sensor head and reflected through the flap back into the sensor head, and a measurement of a Q factor is obtained in step 308. That is, a parameter that is constructed from optical measurement data obtained through the sensor head is obtained. A Q factor is effectively a parameter associated with the ratios of optical measurements taken using the sensor head.

Generally, the best approximate location for obtaining measurements of oxygen saturation levels may be a location in which a plurality of ratios of optical measurements all substantially equal one. By way of example, for a system with two sources and four detectors as shown in FIG. 2B, a Q factor may be defined as follows for each wavelength at which light is transmitted by the sources:

$$Q_\lambda = \left[ \frac{U_{S_1 D_1}}{U_{S_1 D_2}} \frac{U_{S_2 D_2}}{U_{S_2 D_1}} \frac{U_{S_2 D_3}}{U_{S_2 D_4}} \frac{U_{S_1 D_4}}{U_{S_1 D_3}} \right]_\lambda$$

where $\lambda$ is a wavelength, $U_{S_1 D_1}$ is an optical measurement at a detector D1 when a source S1 with a wavelength of $\lambda$ is on, and $U_{S_2 D_2}$ is an optical measurement at detector D1 when source S2 with a wavelength of $\lambda$ is on, etc. When each of the ratios has an approximate value of one, the location at which that occurs may be considered to be a best approximate location for obtaining measurements. The indication is that the sensor head is in good contact with tissue, that the tissue is highly homogenous, and that the oximeter of which the sensor head is a part is in good working order. It should be appreciated that for each wavelength, there may be a corresponding Q factor. Hence, for a system in which there are two wavelengths of light produced by light sources, there are two Q factors.

Returning to step 308, after a Q factor or Q factors are measured, then process flow proceeds to step 312 in which it is determined if the Q factor or Q factors indicates that the current location of the sensor head is a best approximate location. That is, it is determined if a Q factor has a value of approximately one. If the indication is that the sensor head is in a best approximate location, the location at which the sensor head is positioned is selected in step 316 as the location to be used in reading oxygen saturation levels. Once the location is selected, the process of selecting a location is completed.

Alternatively, if it is determined in step 312 that the Q factor does not indicate a best approximate location, the implication is that the Q factor has a value that is not approximately equal to one. As such, in step 320, it is determined whether the Q factor is the best obtained Q factor. Such a determination may be based on whether the Q factor obtained via measurements in step 308 has a value that is closest to one of all previously obtained Q factors. If it is determined that the Q factor is the best obtained Q factor, then it is noted in step 324 that the Q factor is the best obtained Q factor. Further, the location associated with the Q factor is noted, e.g., stored in a memory. Then, in step 328, a determination is made as to whether there are more locations to test, i.e., to identify a best approximate location for obtaining readings of oxygen saturation levels.

If the determination in step 328 is that there are more locations to test, then process flow returns to step 304 in which the sensor head is positioned at a new location on the flap. Alternatively, if it is determined that there are no more locations to test, the location associated with the best Q factor is selected in step 332 as the location to be used in reading oxygen saturation levels. After the location is selected, the process of selecting a location is completed.

Returning to step 320, if it is determined that the Q factor obtained in step 308 is not the best obtained Q factor, the indication is that a previously obtained Q factor identified a better location for obtaining readings than the current location at which the sensor head is placed. Accordingly, process flow moves directly to step 328 and a determination of whether there are more locations to test.

Figure 4:
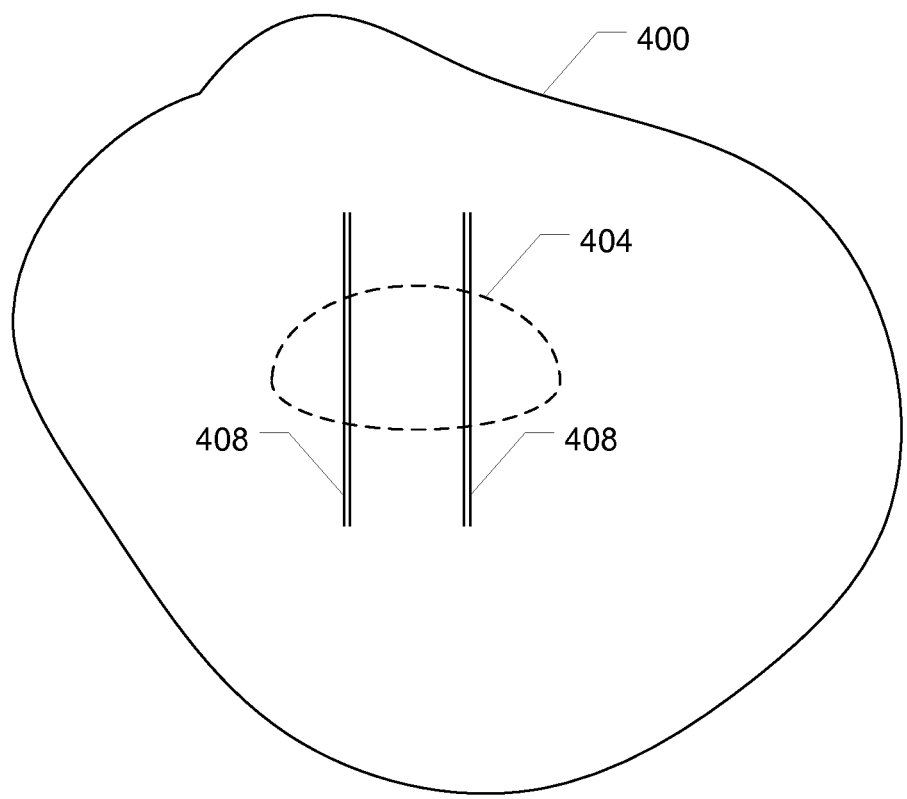
FIG. 4 is a diagrammatic representation of flap tissue in a body prior to the flap tissue being at least partially cut from the body in accordance with an embodiment of the present invention.

When there is an adequate blood supply provided to a transplanted flap, the survivability of the transplanted flap is generally increased. Blood is supplied via an artery or arteries to the transplanted flap. In order for blood to be supplied to a flap after transplant surgery, the flap itself is generally coupled to at least one artery that is, in effect, severed when the flap is removed from a donor site. FIG. 4 is a diagrammatic representation of a flap in a body prior to the flap being at least partially cut from the body in accordance with an embodiment of the present invention. Within a body 400 at a donor location, a flap 404 may be defined, i.e., a flap that is to be removed for transplant to a different location within body. Typically, flap 404 may include one or more arteries 408 that run therethrough and supply oxygenated blood to flap 404. When potential flap 404 is removed, at least one of arteries 408 is typically preserved for use in supplying blood to flap 404 when flap 404 is transplanted to a new location.

Oxygen saturation levels may be measured with respect to a potential flap at a donor site in a body to identify an artery which may be tied off once the potential flap is removed, as well as to identify an artery which may be used as a reattachment artery to supply blood to the flap once the flap is transplanted into a new site in the body. In other words, oxygen saturation levels may be used to characterize arteries in a flap during a flap removal process. A reattachment artery is generally an artery that is coupled to a flap and may be attached, as for example using microsurgery techniques, to another artery at a new site in the body to provide flood flow to the flap. By properly identifying a suitable reattachment artery before the reattachment artery is attached to an artery at a new site, the likelihood of compromising the flap is reduced, as the designated reattachment artery would likely provide an adequate supply of blood to the flap.

Figure 5:
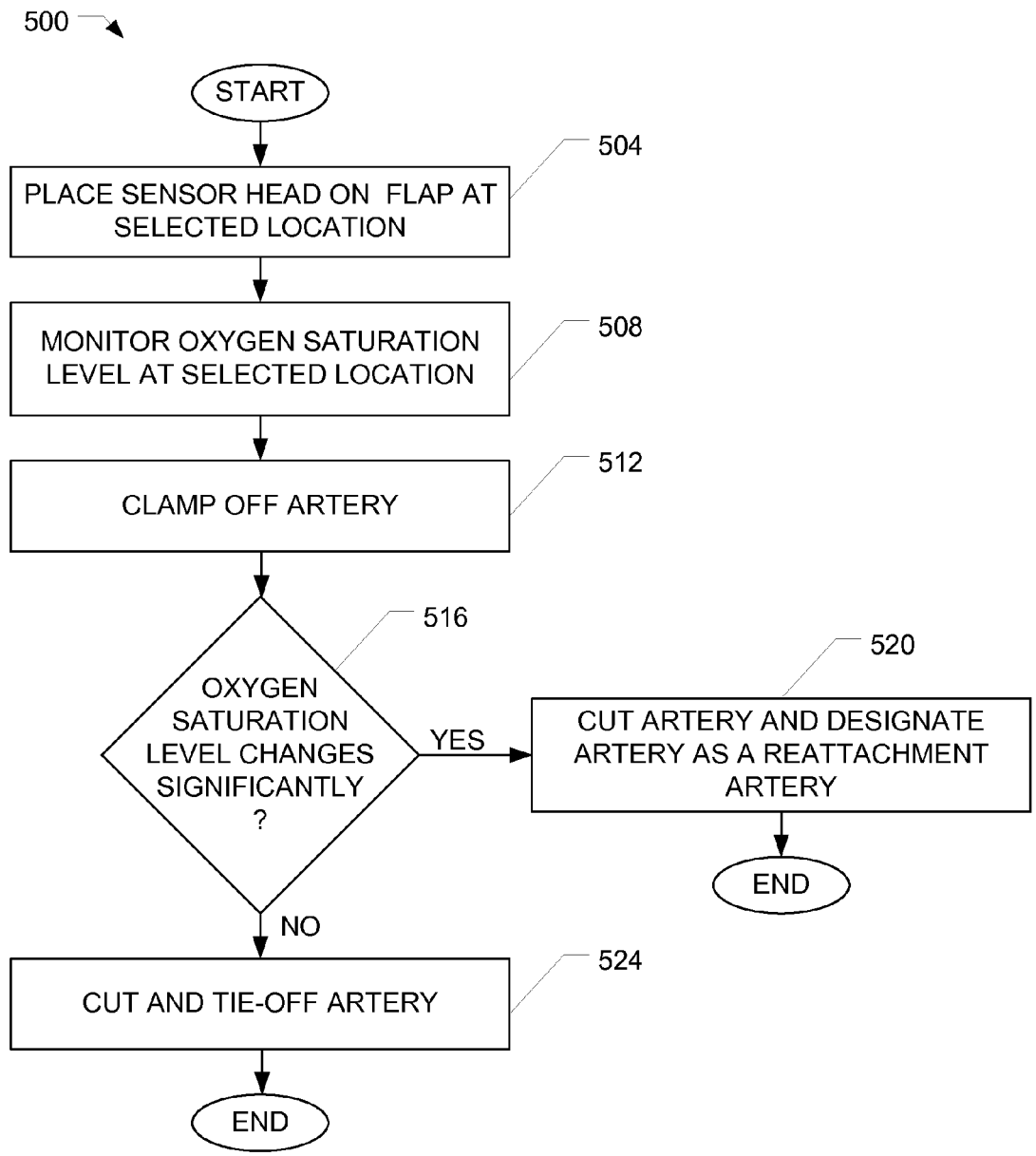
FIG. 5 is a process flow diagram which illustrates one method of utilizing an oximeter to identify an artery in potential flap tissue which may be suitable for use as a reattachment artery in accordance with an embodiment of the present invention.

Referring next to FIG. 5, the steps associated with one method of utilizing an oximeter to characterize an artery in a flap that is to be removed from a host site of a body will be described in accordance with an embodiment of the present invention. A process 500 of characterizing an artery begins at step 504 in which a sensor head, i.e., a sensor head associated with an oximeter apparatus, is placed on a potential flap at a selected location. The selected location may be substantially any suitable location. Suitable locations may include, but are not limited to, a location on the flap at which a Q factor has a value of approximately one or a location that is relatively distant from an artery that is believed to provide significant blood supply to the flap. In step 508, the oxygen saturation level at the selected location is monitored, as for example substantially continuously by maintaining contact between the sensor head and a top surface of the flap.

After the oxygen saturation level at the selected location is monitored, e.g., monitored long enough to determine a substantially steady-state oxygen saturation level, an artery that supplies blood to the flap is clamped off or otherwise pinched off in step 512. Once the artery is clamped off, and blood flow to the flap via the artery is effectively terminated, it is determined in step 516 whether the monitored oxygen saturation level changes significantly. That is, a determination is made as to whether there is a significant drop in the monitored oxygen level at the selected location. In general, a drop of approximately twenty percent or more in an oxygen saturation level, e.g., from approximately fifty percent to approximately thirty percent, is considered to be a significant drop, though the percentage drop may vary.

If it is determined that there is a significant change in the oxygen saturation level, the indication is that the artery is likely to supply a significant amount of blood to the flap. As such, the artery may be appropriate as an artery to use as a reattachment artery, i.e., as an artery that may be attached to another artery near a transplant site to provide a blood supply to the flap, when the flap is transplanted. Hence, in step 520, the artery is cut and is designated as a reattachment artery. After the artery is cut, the process of characterizing the artery is completed.

Returning to step 516, if it is determined that the oxygen saturation level at the selected location does not change significantly in response to the artery being clamped off, the implication is that the artery is not a significant provider of blood to the flap. Therefore, process flow moves from step 516 to step 524 in which the artery is cut and tied off. Once the artery is cut and tied off, the process of characterizing the artery is completed.

Figure 6A:
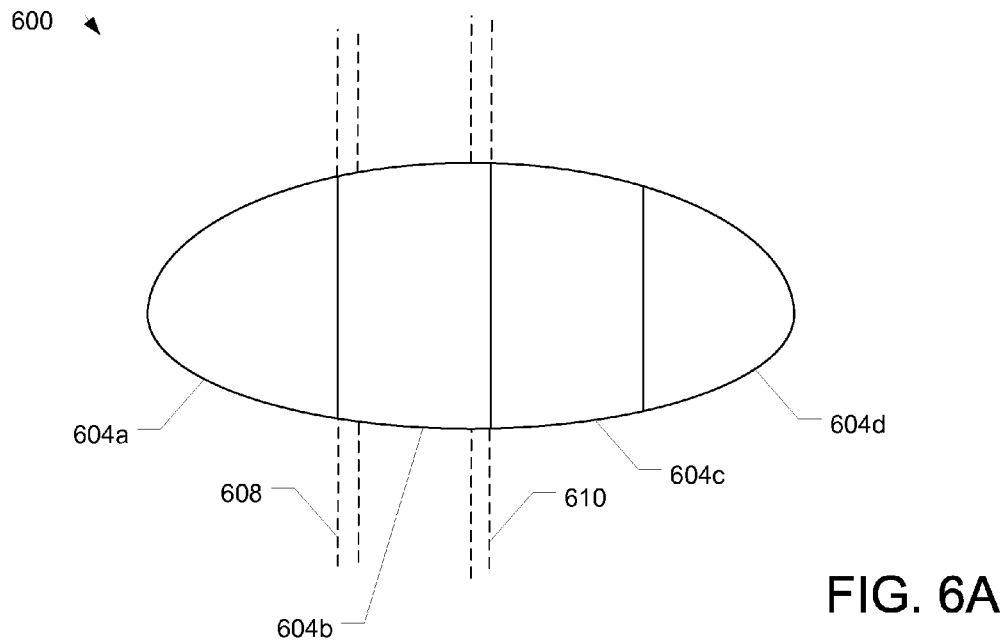
FIG. 6A is a diagrammatic representation of a flap in accordance with an embodiment of the present invention.

Flaps may generally be of a variety of different sizes and shapes, depending upon the intended use for the flaps. By way of example, a transverse rectus abdominal muscle (TRAM) flap may be sized for use in creating a breast. FIG. 6A is a diagrammatic representation of a TRAM flap in accordance with an embodiment of the present invention. A TRAM flap 600 generally includes zones 604*a-d*, and has an artery 608 and a vein 610 running substantially therethrough. When TRAM flap 600 is transplanted into a donor site, artery 608 and vein 610 may be substantially stitched to an artery and a vein at the donor site to allow blood to flow through TRAM flap 600.

Figure 6B:
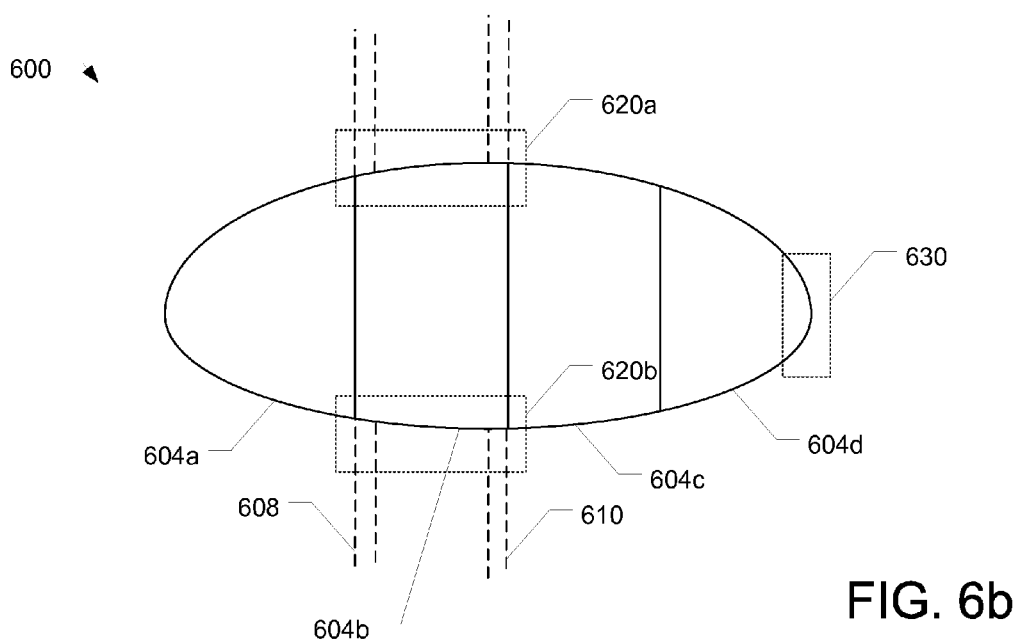
FIG. 6B is a diagrammatic representation of locations at which oxygen saturation readings may be taken with respect to a flap, i.e., flap 600 of FIG. 6A, in accordance with an embodiment of the present invention.

Typically, a zone 604*b* is the most oxygenated zone in TRAM flap 600, as artery 608 passes therethrough. However, other portions of TRAM flap 600 may effectively be poorly supplied if oxygenated blood does not flow efficiently in those portions. Although monitoring portions 620*a*, 620*b* in the vicinity of zone 604*b*, as indicated in FIG. 6B, may allow the oxygen saturation levels in zone 604*b* to be assessed, as zone 604*b* is generally highly oxygenated, monitoring portions 620*a*, 620*b* may not provide an accurate assessment of whether TRAM flap 600 is viable.

In one embodiment, the oxygen saturation levels of all zones 604*a-d* may be monitored to effectively assess the blood supply of TRAM flap 600. By assessing the oxygen saturation levels at different location, i.e., by spot checking the oxygen saturation levels, the viability of TRAM flap 600 may be more accurately assessed. If an area is identified as being poorly supplied, that area may be trimmed or otherwise removed in an effort to preserve the overall integrity of TRAM flap 600. It has been observed that by monitoring an area 630 that is distal to artery 608, any blood supply problems in TRAM flap 600 may generally be identified. That is, monitoring the oxygen saturation level of a location or area 630 that is furthest from a known blood supply, e.g., artery 608, typically allows any blood supply problems to be readily identified.

Figure 7:
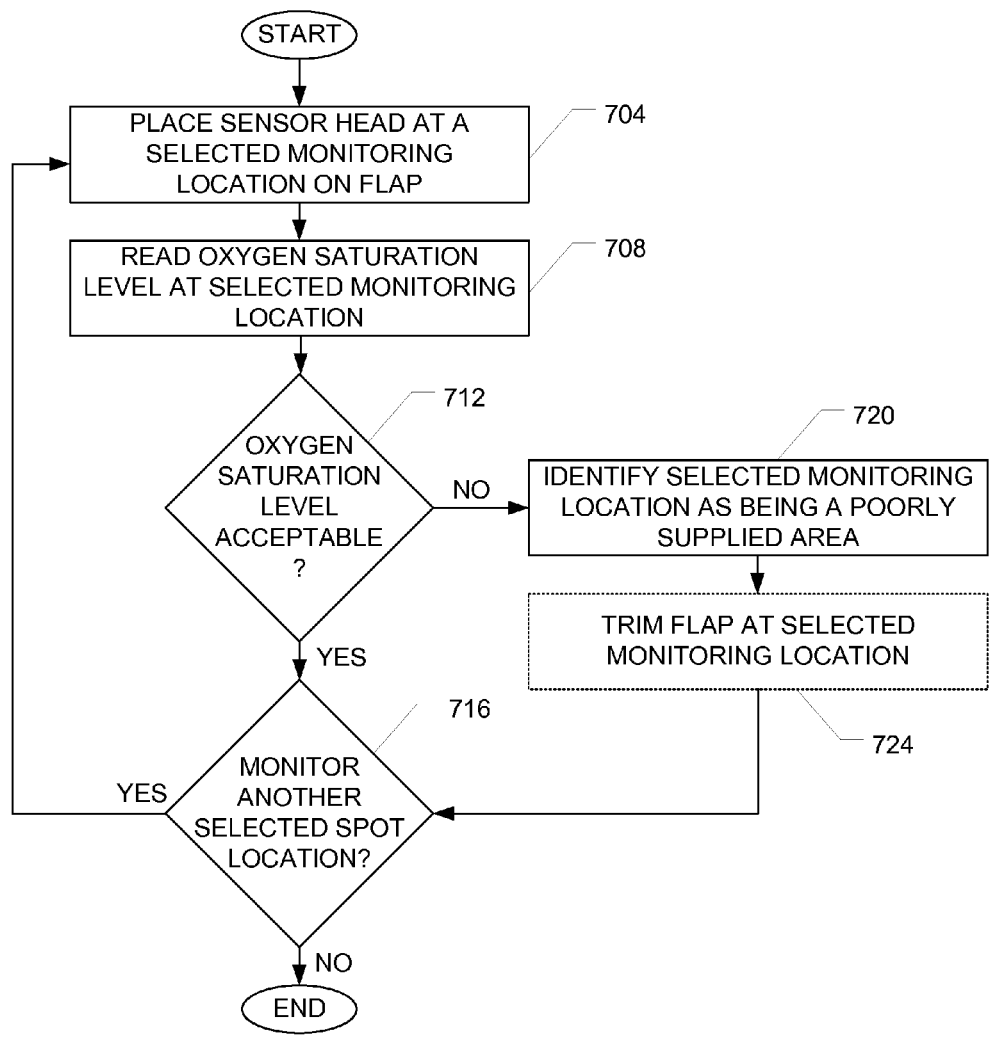
FIG. 7 is a process flow diagram which illustrates one method of using an oximeter to identify poorly supplied areas in transplanted flap tissue in accordance with an embodiment of the present invention.

FIG. 7 is a process flow diagram which illustrates one method of using an oximeter to identify poorly supplied areas in transplanted flap in accordance with an embodiment of the present invention. A process 700 of identifying an area of a flap with a relatively poor blood supply begins at step 704 in which a sensor head of an oximeter is placed at a selected monitoring location on a flap. The selected monitoring location may generally be substantially any location on the flap. The selected monitoring location may be, but is not limited to being, a location for which a Q factor has a value of approximately one or a location that is furthest from a known blood supply on the flap.

After the sensor head is placed at a selected monitoring location, the oxygen saturation level at the selected monitoring location is read in step 708. A determination is then made at step 712 as to whether the oxygen saturation level is acceptable. An acceptable oxygen saturation level may be in the range of between approximately 50 percent and approximately 100 percent, although it should be appreciated that an oxygen saturation level that is considered to be acceptable may vary widely. A marginally acceptable oxygen saturation level may be in the range of between approximately 30 percent and approximately 50 percent.

If it is determined that the oxygen saturation level is acceptable, the indication is that the selected monitoring location is not poorly supplied. Accordingly, process flow proceeds to step 716 in which it is determined whether the oxygen saturation level at another selected location is to be monitored. If it is determined that no other location is to be monitored, the process of identifying an area of a flap with a relatively poor blood supply is terminated. Alternatively, if it is determined in step 716 that the oxygen saturation level at another location is to be monitored, process flow returns to step 704 in which the sensor head is positioned at a new selected monitoring location on the flap.

Returning to step 712, if the determination is that the oxygen saturation level at the selected monitoring location is not acceptable, then the selected monitoring location is identified as being a poorly supplied area in step 720. In one embodiment, once the selected monitoring location is identified as being a poorly supplied area, the flap may be trimmed at the selected monitoring location in step 724. After the flap is trimmed or, if the flap is not trimmed, after the selected monitoring location is identified as a poorly supplied area, process flow then moves to step 716 in which it is determined whether the oxygen saturation level at another location is to be monitored.

Although only a few embodiments of the present invention have been described, it should be understood that the present invention may be embodied in many other specific forms without departing from the spirit or the scope of the present invention. By way of example, flaps have generally been described as being removed from a donor site for transplant to a new site. However, flaps may instead be substantially only partially removed from a donor site for transplant to a new site that may be a part of or adjacent to the donor site. In other words, in lieu of being a microvascular free flap, a flap may instead be a musculocutaneous, a regional flap, or a local flap. Further, the methods described above are not limited to use in flap surgeries, e.g., the methods described above may be applied to digit replantation surgeries.

Substantially any optical imaging system may be used to monitor oxygen saturation levels. For instance, substantially any oximeter may be used to obtain readings of oxygen saturation levels. In one embodiment, the oximeter may be the ODISsey Tissue Oximeter available commercially from ViOptix, Inc. of Fremont, Calif.

The steps associated with the various methods of the present invention may be widely varied. Steps may be added, altered, removed, and reordered without departing from the spirit or the scope of the present invention. By way of example, instead of monitoring a single location on a flap to characterize an artery, a plurality of locations on a flap may be monitored to characterize an artery. Therefore, the present examples are to be considered as illustrative and not restrictive, and the invention is not to be limited to the details given herein, but may be modified within the scope of the appended claims.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for assessing viability of flap tissue, the method comprising:
　positioning a sensor head of a probe at a first location of the flap tissue, wherein the probe comprises a cable having a connector adapted to be removably coupled to a console, the sensor head comprises a first source structure and first detector structure, the first source structure and first detector structure are positioned on a planar surface of the sensor head, and a beam combiner is external to the probe;
　causing a first light signal to be transmitted through a first optical fiber in the probe to the first source structure and into the flap tissue;
　after the causing the first light signal, and without repositioning the sensor head of the probe, allowing the first detector structure to receive a reflection of the first light signal from the flap tissue, the reflection being a second light signal; and
　enabling transmitting of the second light signal from the first detector structure through a second optical fiber in the probe to the connector adapted to be removably coupled to the console,
　whereby the console, based on the first and second light signals, causes a screen of the console to display a first indication of an oxygen saturation level representative of the first location of the flap tissue,
　whereby the console causes a second indication of the oxygen saturation level representative of the first location of the flap tissue as being greater than a predetermined oxygen saturation level, indicative of a viability of the flap tissue, and
　whereby the console causes a third indication of the oxygen saturation level representative of the first location of the flap tissue as being less than the predetermined oxygen saturation level, indicative of a viability of the flap tissue, wherein the third indication is different from the second indication.

2. The method of claim 1 wherein the planar surface of the sensor head comprises at least four detector structures, arranged in a line, and at least two source structures, not arranged in the line.

3. The method of claim 1 wherein the cable is a single cable of the probe and the first and second optical fibers are within the single cable.

4. The method of claim 3 wherein the single cable extends from the connector adapted to be removably coupled to the console to the sensor head.

5. The method of claim 1 wherein cross-sectional areas of the first and second optical fibers are the same.

6. The method of claim 1 wherein before the causing a first light signal to be transmitted, the method comprises removably coupling the connector of the cable to the console.

7. The method of claim 1 wherein the causing a first light signal to be transmitted comprises causing the first light signal to be transmitted from the console and through the connector to the first source structure; and
　the enabling transmitting of the second light signal comprises enabling the second light signal to be transmitted from the first detector structure and through the connector to the console.

8. The method of claim 1 wherein when the console causes the second indication, the method comprises trimming the flap tissue at the first location.

9. The method of claim 1 comprising:
　after the causing a first light signal to be transmitted, causing a third light signal, which is at a different wavelength from the first light signal, to be transmitted through the first optical fiber in the probe to the first source structure and into the flap tissue.

10. The method of claim 9 wherein the third light signal passes through the beam combiner, coupled to the first optical fiber, and the beam combiner is outside of the probe and sensor head.

* * * * *